United States Patent [19]

Katsuyama

[11] Patent Number: 5,186,894
[45] Date of Patent: Feb. 16, 1993

[54] DRY ANALYSIS ELEMENT FOR THE ANALYSIS OF IRON IONS

[75] Inventor: Harumi Katsuyama, Asaka, Japan

[73] Assignee: Fuji Photo Film Co, Ltd., Kanagawa, Japan

[21] Appl. No.: 780,740

[22] Filed: Oct. 18, 1991

[30] Foreign Application Priority Data

Oct. 20, 1990 [JP] Japan .................................. 2-282316

[51] Int. Cl.$^5$ .............................................. G01N 31/22
[52] U.S. Cl. ........................................ 422/56; 436/74; 436/78; 436/84; 436/170; 436/175
[58] Field of Search ............... 436/74, 78, 84, 170, 436/175; 422/56-58

[56] References Cited

U.S. PATENT DOCUMENTS 4,810,656 3/1989 Torelli .............................. 436/84 X
5,017,498 5/1991 Fossati et al. ......................... 436/84

FOREIGN PATENT DOCUMENTS 0147660 7/1985 European Pat. Off. .
0296795 12/1988 European Pat. Off. .

OTHER PUBLICATIONS

Chemical Abstracts, vol. 108, No. 15, Apr. 11, 1988, Columbus, Ohio, US. Abstract No. 127912-A Sensitive Direct Colorimetric Assay of Serum Ion Using the Chromogen, Nitro-PAPS-p. 393.
Chemical Abstracts, vol. 114, No. 25, Jun. 24, 1991, Columbus, Ohio, US. Abstract No. 243746-A Sensitive Direct Colorimetric Assay of Serum Zinc Using the Nitro-PAPS and Microwell Plates-p. 414.

Primary Examiner—Jill A. Johnston
Attorney, Agent, or Firm—McAulay Fisher Nissen Goldberg & Kiel

[57] ABSTRACT

A dry analysis element for the analysis of iron ions, which is improved in selectivity so that iron ions can be analyzed reliably at a high sensitivity without the interferences by the presence of hindering $Cu^{2+}$ and/or $Zn^{2+}$ ions. The analysis element comprises a detection reagent layer containing Nitro-PAPS acting as a chelating agent and a cationic compound, and a pre-treating layer containing a $Cu^{2+}$-specific chelating agent. The analysis element further includes a pH buffer for keeping the pH value of the detection reagent layer within the range of from pH 3.0 to 5.0. The pH adjusting buffer may be contained in either one of the detection reagent layer or the pre-treating layer, or may be contained in another layer. The detection reagent layer may be composed of a coloring reagent layer containing Nitro-PAPS acting as the chelating agent, and a diffusion-preventing layer laminated on the coloring reagent layer and containing the cationic compound.

10 Claims, 1 Drawing Sheet

DRY ANALYSIS ELEMENT FOR THE ANALYSIS OF IRON IONS

BACKGROUND OF THE INVENTION

1. Field of the Invention

The present invention relates to a dry analysis element for the analysis of iron ions in an aqueous liquid sample. Particularly, it relates to a dry analysis element which is suited for the analysis of ferrous ions ($Fe^{2+}$) in the presence of cupric ions ($Cu^{2+}$) and zinc ($Zn^{2+}$).

2. Prior Art

Various methods have been known in the art to analyze the content of iron ions in living body fluids, such as blood, plasma, serum and urine. For example, iron ions in the human serum have been analyzed in the clinical tests for the diagnosis of anemia, liver troubles or lead poisoning.

The atomic adsorption method is the best method for the analysis of the content of iron ions because it has the superior accuracy and sensitivity. However, this method requires a special apparatus and skillfulness and is time consuming method, and thus it is not suited for the practice of analysis in a clinical laboratory or sickroom room of a hospital. The chelatometoric analysis, wherein a chelate compound forming a coloring complex with an iron ion is used, has been widely used as the clinical test.

Various chelating agents have been known for forming complexes with ferrous ions ($Fe^{2+}$). Remarkable progress has been made in development of the chelating agents for use in detection of $Fe^{2+}$ ions. For instance, although the conventionally known complex of o-phenanthroline or Ferrozine and $Fe^{2+}$ ions has a molecular extinction coefficient ranging from $1 \times 10^{-4}$ to $3 \times 10^{-4}$ $mol^{-1} cm^{-1}$, complexes of the derivative of pyridylazo compounds developed by Shibata et al. "Bunseki-Kagaku" (Analytical Chemistry), 23, 1412-1430 (1974)) have the molar extinction coefficients of higher than the range of $7 \times 10^{-4}$ to $10 \times 10^{-4}$ $mol^{-1} cm^{-1}$ to remarkably improve the sensitivity for the detection of ferrous ions.

With the development of such chelating agents which provide high sensitivity in detection of ferrous ions, it has been tried to analyze ferrous ions in so-called dry methods in lieu of the conventional wet methods, which are simple in construction and operation. In so-called wet method, a reagent is once dissolved in an aqueous medium to prepare a reagent solution, to which a sample to be analyzed is added and a formed coloring product is measured through a colorimeter. On the contrary, in dry method, an aqueous sample is directly spotted on a dry analysis element composed of a test piece, analysis slide or analysis tape containing a reagent composition in a dry state, and the degree of a coloring matter in the dry analysis element is colorimetrically determined. Accordingly, the dry analysis methods are superior over the wet system, since the former provide a result of analysis by a simple operation within a short time.

One example of such a dry analysis element for the analysis of iron ions is disclosed in Unexamined Japanese Patent Publication No. 21368/1989 (corresponding to U.S. Pat. No. 4,789,525 and EP 0 296 795A; meantime throughout this specification, numbers in the parentheses following to Japanese Publication Nos. indicate coresponding foreign Publications).

In dry method for the analysis of ferrous ions, it is required that (1) the molecular extinction coefficient of the formed complex of ferrous ion and chelating agent is high enough for providing a satisfactory sensitivity, that (2) the reaction rate for forming the complex is sufficiently high not to spoil the simplicity and prompt response of dry analysis method, and that (3) the reaction has a high selectivity to exclude the influence by other interfering or hindering ions. In general, chelating agents forming complexes with ferrous ions also form coloring complexes with cupric ($Cu^{2+}$) and zinc ions ($Zn^{2+}$). The blood serum of a normal human being contains 90 to 180 µg/dl of $Fe^{2+}$, 100 to 200 µg/dl of $Cu^{2+}$ and 90 to 120 µg/dl $Zn^{2+}$, the contents of $Cu^{2+}$ and $Zn^{2+}$ being comparable to the content of $Fe^{2+}$. Accordingly, when the content of ferrous ions in a human blood serum sample is analyzed, the slectivity to ferrous ions against the reactions of these interfering ions is an important factor.

In the prior art dry analysis element disclosed in Unexamined Japanese Patent Publication No. 21368/1989, a pyridylazo compound is used as the chelating agent for forming a chelate complex with iron ions ($Fe^{2+}$). The pyridylazo compound used in this prior art dry analysis element is an oil-soluble chelating agent and combined with a coupler solvent (oil) having a high dielectric constant for allowing impregnation with polar ions to exclude interferences by the co-existing $Cu^{2+}$ and $Zn^{2+}$ ions. However, interferences by these hindering ions cannot be excluded or suppressed to a satisfactorily low level at the pH (4 to 5) condition under the practical use. In order to preclude $Cu^{2+}$ ions, a chelating agent, such as neocuproine, is used together. However, the interference by $Zn^{2+}$ ions which form a complex having a relatively high molecular extinction coefficient under the practical pH condition cannot be excluded to a satisfactorily low level.

Furthermore, since an oil-soluble chelating agent is used in the prior art technology, there arises a problem that the reaction of the used chelating agent and hydrophilic $Fe^{2+}$ ions is retarded.

OBJECT AND SUMMARY OF THE INVENTION

An object of this invention is to provide a dry analysis element for the analysis of iron ions, which has a high sensitivity and selectivity to iron ions to give prompt response to $Fe^{2+}$ ions while eliminating the interferences by hindering $Cu^{2+}$ and $Zn^{2+}$ ions.

The object of this invention is achieved by the provision of a dry analysis element for the analysis of iron ion, comprising:

(a) a detection reagent layer containing Nitro-PAPS acting as a chelating agent and a cationic compound;

(b) a pre-treating layer containing a chelating agent specifically forming a coordination compound (complex) with cupric ion; and (c) a pH adjusting buffer for keeping the pH value of said detection reagent layer within the range of from pH 3.0 to pH 5.0, said pH adjusting buffer being contained in either one of said detection reagent layer or said pre-treating layer or contained in another layer.

The dry analysis element for the analysis of iron ions, according to this invention, is principally used for the analysis of ferrous ions ($Fe^{2+}$). However, this analysis element may be used for the analysis of ferric ions ($Fe^{3+}$) when a reducing agent for reducing ferric ions ($Fe^{3+}$) to ferrous ions ($Fe^{2+}$) is contained in the pre-treating layer. By using the dry analysis element having the pre-treating layer containing such a reducing agent, the total content of iron ions, including $Fe^{2+}$ and $Fe^{3+}$ ions, may also be determined.

In the present invention, Nitro-PAPS (Chemical Name: 2-(5-Nitro-2-pyridylazo)-5-(N-propyl-N-sulfopropylamino)phenol disodium salt, dihydrate; CAS Registry No. 113516-70-4) is used as the chelating agent for forming a coloring complex with $Fe^{2+}$ ions. Nitro-PAPS has a high detection sensitivity and forms a complex having an extremely high molar extinction coefficient.

According to an important feature of the invention, the interference by hindering $Zn^{2+}$ ions is eliminated by keeping the pH value within the range of from pH 3.0 to pH 5.0. On the other hand, the interference by the hindering $Cu^{2+}$ is eliminated by the pre-treating layer which contains a $Cu^{2+}$-specific chelating agent.

According to another important feature of the invention, a cationic compound is contained in the detection reagent layer to prevent migration of Nitro-PAPS from the detection reagent layer to the pre-treating layer so that formation of a complex of Nitro-PAPS and $Cu^{2+}$ ion in the pre-treating layer is obviated.

Figure 1:
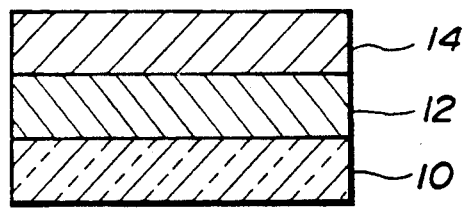
FIG. 1 is a sectional view showing the layer construction of an embodiment of the dry analysis element of the invention.

DETAILED DESCRIPTION OF PREFERRED EMBODIMENTS (1) Principal Layer Structure of the Analysis Element Referring to FIG. 1 showing an embodiment of the invention, a light-transmitting support is denoted by 10, on which a detection reagent layer 12 and a pre-treating layer 14 are laminated.

The pre-treating layer 14 is composed of a water permeable layer and contains a chelating agent which specifically forms a coordination compound (complex) with cupric ion, so that $Cu^{2+}$ ions which might be present in the aqueous liquid sample to hinder analysis of iron ions are trapped to be removed from the aqueous liquid sample. In a preferred embodiment, the pre-treating layer may contain a reducing agent for reducing $Fe^{3+}$ ions to $Fe^{2+}$ ions.

The detection reagent layer 12 is composed of a water permeable layer and contains Nitro-PAPS acting as a chelating agent and a cationic compound.

A pH buffer reagent or buffer composition for keeping the pH value within the range of pH 3.0 to pH 5.0 is contained in either one of the pre-treating layer 14 or the detection reagent layer 12. Preferably, the pH buffer reagent is contained in the detection reagent layer 12 where a complex is formed by the reaction between Nitro-PAPS and $Fe^{2+}$ ions.

Figure 2:
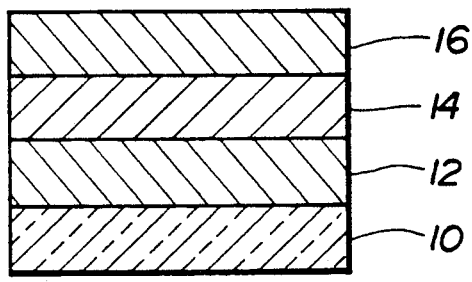
FIG. 2 is a sectional view showing the layer construction of another embodiment of the dry analysis element of the invention.

FIG. 2 shows a second embodiment which comprises a spreading layer 20 laminated on the pre-treating layer 14.

Figure 3:
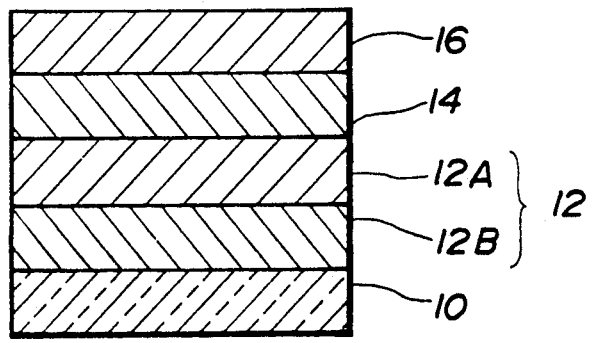
FIG. 3 is a sectional view showing the layer construction of a further embodiment of the dry analysis element of the invention.

FIG. 3 shows a third embodiment. In this embodiment, the detection reagent layer 12 includes a coloring reagent layer 12A in which the chelating agent Nitro-PAPS is contained, and a diffusion-preventing layer 12B containing a cationic compound.

The layers of the analysis element are substantially in fluid contact with each other so that low molecular weight components in the sample liquid picked up from a living fluid and spotted on the analysis element can freely diffuse or migrate between these layers. However, as will be described hereinafter, Nitro-PAPS contained in the detection reagent layer is prevented from migrating from the detection reagent layer to other layers due to the presence of the cationic compound.

Each layer may contain a hardener, surface active agent or buffer. An adhesive layer may be interposed between the adjacent layers.

The structures of respective layers will be described below.

(2) Spreading Layer

The spreading layer is a layer having a so-called metering function for spreading a liquid sample within an area in proportion to the volume of the liquid sample spotted on the analysis element, and composed of a porous material.

This porous spreading layer may be fibrous or non-fibrous.

Examples of fibrous porous spreading layer include a spreading layer made of a woven fabric as disclosed in Unexamined Japanese Patent Publication Nos. 164356/1980 (U.S. Pat. No. 4,292,272) and 66359/1982 (U.S. Pat. No. 4,783,315), a spreading layer made of a knitted fabric as disclosed in Unexamined Japanese Patent Publication No. 222769/1985 (EP 0162302A), a spreading layer made of paper prepared from a pulp containing an organic polymer as disclosed in Unexamined Japanese Patent Publication No. 148250/1982, and a spreading layer formed by coating a dispersion of fibers and a hydrophilic polymer as disclosed in Unexamined Japanese Patent Publication No. 125847/1982 (U.S. Pat. No. 4,594,224).

Examples of non-fibrous porous spreading layer include non-fibrous isotropic porous spreading layers such as a membrane filter layer (blush polymer layer) and an isotropically porous spreading layer containing open cellular micropores (layer having three-dimensional lattice structure composed of micro particles) made of micro particles such as polymer microbeads bound through point contact by a hydrophilic polymer binder. These isotropically porous layers are disclosed in Japanese Patent Publication No. 21677/1978 (U.S. Pat. No. 3,992,158) and Unexamined Japanese Patent Publication No. 910859/1980 (U.S. Pat. No. 4,258,001).

Preferable spreading layers are made of woven or knitted fabrics. The woven or knitted fabric may be subjected to glow discharge treatment as disclosed in Unexamined Japanese Patent Publication No. 66359/1982 (U.S. Pat. No. 4,783,315). In order to control the spreading area or spreading rate, a hydrophilic polymer or surface active agent may be contained in the spreading layer as disclosed in Unexamined Japanese Patent Publication No. 222770/1985 (corresponding to EP 0162301A), Unexamined Japanese Patent Publication No. 219397/1988 (corresponding to German Patent Laid-Open Publication DE 37 17 913A), Unexamined Japanese Patent Publication No. 112999/1988 (corresponding to German Patent Laid-Open Publication DE 37 17 913A) and Unexamined Japanese Patent Publication No. 182652/1987 (corresponding to German Patent Laid-Open Publication DE 37 17 913A).

(3) Detection Reagent Layer

The detection reagent layer 12 contains Nitro-PAPS acting as a chelating agent and a cationic compound.

(3-1) Nitro-PAPS

Nitro-PAPS is an abridgement of the chemical name 2-(5-Nitro-2-pyridylazo)-5-(N-propyl-N-sulfopropylamino) phenol disodium salt, dihydrate (CAS Registry No. 113516-70-4), and represented by the following chemical formula:

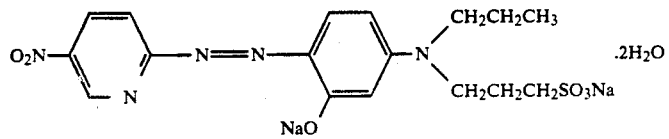

Nitro-PAPS is a compound having an electron withdrawing group and an electron donating group at the terminal ends of the para position of the azo group, and thus capable of forming polar sructure to show a sensitive coloring change by forming a complex with a metal. The pH ranges of this compound for forming complexes with respective metals, the maximum absorption wavelengths $\lambda_{max}$ and the molar extinction coefficients $\epsilon$ of the chelate complexes with respective metals are shown below.

| Metal | pH Range | $\lambda_{max}$ | Molecular Extinction Coefficient $\epsilon$ ($\times 10^4$ mol$^{-1}$ cm$^{-1}$) |
|---|---|---|---|
| Fe(II) | 3 to 7.5 | 582 | 10.7 |
| Cu(II) | 2 to 5.0 | 566 | 7.1 |
| Zn(II) | 7.5 to 9.0 | 566 | 15.0 |

In the present invention, a pH buffer for keeping the pH value of the analysis element under the practical condition within the range of from 3.0 is 5.0 is used. Accordingly, formation of a complex with $Zn^{2+}$ is prevented.

On the other hand, although $Cu^{2+}$ can form a complex within this pH range (pH 3.0 to 5.0), $Cu^{2+}$ ions are removed by the addition of a chelating agent having a specific affinity with $Cu^{2+}$, as will be described in detail hereinafter.

(3-2) Cationic Compound

The cationic compound bonds electrostatically to Nitro-PAPS which is an anionic compound, so that Nitro-PAPS is prevented from migrating to the layers (particularly to the pre-treating layer 14) other than the detection reagent layer 12. If Nitro-PAPS diffuses or spreads to migrate into the pre-teating layer 14 laminated over the detection reagent layer 12, the migrating Nitro-PAPS reacts with $Cu^{2+}$ ions trapped within the pre-treating layer 14 to form a complex which has an absorption spectrum overlapped with that of the $Fe^{2+}$/Nitro-PAPS complex to induce a noise or interference. The cationic compound improves the efficiency for the detection of $Fe^{2+}$/Nitro-PAPS complex by preventing such interference reaction.

Since the cationic compound used is the present invention for preventing diffusion or migration of Nitro-PAPS into the pre-treating layer 14, it is not essential to contain the same in the same layer in which Nitro-PAPS is contained. As shown in FIG. 3, a separate layer containing the cationic compound can be laminated as a diffusion-preventing layer 12A on a coloring reagent layer 12B containing Nitro-PAPS. In such an embodiment, the detection reagent layer 12 includes two layers, i.e. the coloring reagent layer 12B and the diffusion-preventing layer 12A.

Examples of the cationic compound which can be used in this invention include low molecular weight compounds each containing a quarterly ammonium ion and polymer compounds (each having a molecular weight of from 5,000 to 200,000, particularly 10,000 to 50,000).

Examples of the low molecular weight cationic compounds are tetrabenzylmethylbenzylammonium chloride, trioctylmethylammonium chloride and tributylammonium chloride.

Cationic polymers which may be used in the present invention will be set forth below.

Vinylpyridinium cation polymers as disclosed in U.S. Pat. Nos. 2,548,564, 2,484,430, 3,148,062 and 3,756,814 and Unexamined Japanese Patent Publication No. 136626/1977 (Chemical Abstracts, 89:34120s);

Polymers which are capable of cross-linking gelatin, as disclosed in U.S. Pat. Nos. 3,625,694, 3,859,096, 4,128,538 and 3,756,824 and British Patent No. 1,277,453;

Aqueous sol type cationic polymers as disclosed in U.S. Pat. Nos. 3,958,995, 2,721,852 and 2,798,063 and Unexamined Japanese Patent Publication Nos. 115228/1979 (GB 2,018,452A), 145529/1979 (Chemical Abstracts, 92:189217q) and 126027/1979 (Chemical Abstracts 92:67704a);

Water-insoluble cationic polymers as disclosed in U.S. Pat. No. 3,958,008 and Unexamined Japanese Patent Publication No. 33172/1980;

Reactive mordants capable of forming covalent bonds with dyes, as disclosed in U.S. Pat. No. 4,168,976 (corresponding to Unexamined Japanese Patent Publication No. 137333/1979); and Cationic polymers as disclosed in U.S. Pat. Nos. 3,709,690, 3,788,855, 3,642,482, 3,488,706, 3,557,066, 3,272,147 and 3,271,148 and Unexamined Japanese Patent Publication Nos. 71332/1975 (U.S. Pat. No. 4,124,386), 30328/1978 (U.S. Pat. No. 4,131,469), 155528/1977 (CA 89:207248v), 125/1978 (U.S. Pat. No. 4,154,615) and 1024/1978 U.S. Pat. No. 4,142,899).

In addition to the cationic polymers set forth above, the cationic polymers disclosed in U.S. Pat. Nos. 2,675,316 and 2,882,156 may also be used.

It is preferred to use a cationic compound which has little intention to migrate from a hydrophilic colloidal layer to other layers. Preferable examples of the cationic compounds are the compounds capable of cross-linking with hydrophilic colloids, such as gelatin, water-insoluble cationic polymers and aqueous sols (or latex dispersions).

Particularly preferable cationic polymers will be specifically set forth below:

(1) Polymers each having a quarterly ammonium group and a group capable of forming a covalent bond with gelatin (for example, aldehyde, chloroalkanoyl, chloroalkyl, vinylsulfonyl, pyridiniumpropionyl, vinylcarbonyl or alkylsulfonoxy group), a specific example is the compound represented by the following formula of:

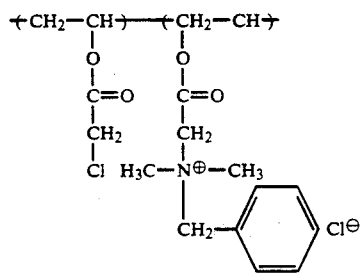

(2) Reaction product of a copolymer having a monomer repeating unit represented by the following general formula (I) and also having a repeating unit of an ethylenically unsaturated monomer and a cross-linking agent (for example bisaklanesulfonate or bisallenesulfonate);

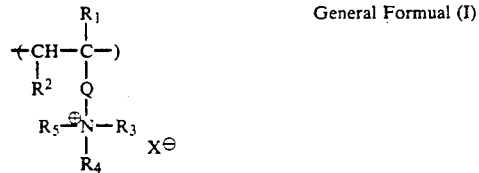
General Formual (I)

wherein $R_1$ stands for hydrogen or an alkyl group; $R_2$ stands for hydrogen or an alkyl group or an aryl group; Q is a divalent group; $R_3$, $R_4$ and $R_5$ each stands for an alkyl group or aryl group or at least two of the groups $R_3$ to $R_5$ may form a hetero ring (each of the alkyl or allyl groups may be substituted); and X is an anion.

(3) Polymers represented by the following general formula (II) of:

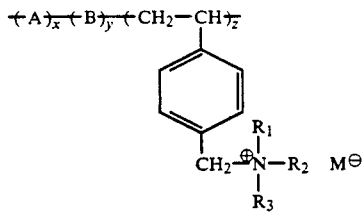

wherein x ranges from about 0.25 to about 5 mol %; y ranges up to about 90 mol %; z ranges from about 10 to about 99 mol %; A stands for a monomer having at least two ethylenic unsaturated bonds; B stands for a copolymerizable ethylenically unsaturated monomer; $R_1$, $R_2$ and $R_3$ each stands for an alkyl group or a cyclic hydrocarbon group, or at least two of the groups $R_1$ to $R_3$ may form a ring (each of these groups or rings may be substituted); and M is an anion.

(4) Water-insoluble polymers having the following repeating unit represented by the general formula (III) in a ratio of not less than ⅓:

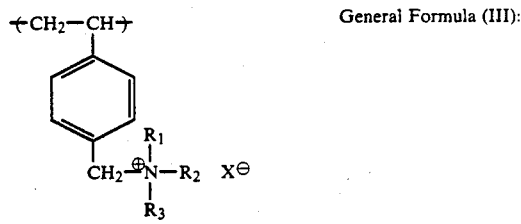
General Formula (III):

wherein $R_1$, $R_2$ and $R_3$ each stands for an alkyl group, the sum of the carbon numbers of the groups $R_1$ to $R_3$ being not less than 12 (each of the alkyl groups may be substituted); and X is an anion.

Other examples of the preferable cationic polymer include the following polymers which are disclosed in Unexamined Japanese Patent Publication No. 89796/1978 (corresponding to U.S. Pat. No. 4,069,017).

(1) Poly(N,N,N-trimethyl-N-vinylbenzylammonium chloride)
(2) Poly(styrene-co-benzyl-(dimethyl)-p-vinylbenzylammonium chloride)
(3) Poly(styrene-co-(vinylbenzyl)-(trihexyl)-ammonium chloride)
(4) Poly(N,N,N-trimethyl-N-vinylbenzylammonium chloride -co-styrene)
(5) Poly(styrene-co-N-vinylbenzyl-N,N-dimethylbenzylammoniumchloride-co-divinylbenzene)

(3-3) Material for the Detection Reagent Layer

In order to ensure the water permeability of the detection reagent layer, the detection reagent layer may be composed of a porous medium similar to that described in the description of the spreading layer. However, it is more preferable to use a hydrophilic polymer binder.

When the detection reagent layer is composed of a water permeable layer made of a hydrophilic polymer binder, examples of the hydrophilic polymers which may be used as the material therefor include gelatin and derivatives thereof (e.g. phthalated gelatin), derivatives of cellulose (e.g. hydroxyethyl cellulose), agarose, sodium alginate, acrylamide copolymers, methacrylamide compolymers, copolymers of acrylamide or methacrylamide with various vinyl monomers, polyhydroxyethyl methacrylate, polyvinyl alcohol, polyvinyl pyrrolidone, sodium polyacrylate and copolymers of acrylic acid with various vinyl monomers.

A detection reagent layer composed of a hydrophilic polymer binder may be prepared by coating an aqueous solution or dispersion containing Nitro-PAPS, a cationic compound, other reagent compositions and a hydrophilic polymer on a support or water-absorbing layer, followed by drying, generally in accordance with the process as disclosed in the specifications of Japanese Patent Publication No. 21677/1988 (corresponding to U.S. Pat. No. 3,992,158), Unexamined Japanese Patent Publication No. 164356/1980 (corresponding to U.S. Pat. No. 4,292,272), Unexamined Japanese Patent Publication No. 101398/1979 (corresponding to U.S. Pat. No. 4,132,528) and Unexamined Japanese Patent Publication No. 292063/1986 (Chemical Abstracts 106, 210567y). The detection reagent layer composed of a hydrophilic polymer binder may have a thickness at the dry state of from about 2 μm to about 50 μm, preferably from about 4 μm to about 30 μm, and a coverage of from about 2 to about 50 g/m$^2$, preferably from about 4 to about 30 g/m$^2$.

The detection reagent layer may contain, in addition to the Nitro-PAPS and the cationic compound, a surface active agent, pH buffer reagent or other additives for improving the coating characteristics, diffusibility of the diffusible material, reactivity and storage stability.

(4) Pre-treating Layer

The pre-treating layer 14 contains a chelating agent which has a specific affinity to form a coordination bond to cupric ion ($Cu^{2+}$). The pre-treating layer 14 may also contain a reducing agent for reducing ferric ion ($Fe^{3+}$) to ferrous ion ($Fe^{2+}$).

The pre-treating layer 14 is composed of a water permeable layer, and may be made of a material similar to that used for forming the detection reagent layer. It is preferred that the pre-treating layer is a substantially non-porous layer made of a hydrophilic polymer binder.

(4-1) $Cu^{2+}$-Specific Chelating Agent

A chelating agent having specific affinity with $Cu^{2+}$ ion is contained in the pre-treating layer so that $Cu^{2+}$ ions are trapped in the pre-treating layer to prevent the reaction between $Cu^{2+}$ ion and Nitro-PAPS in the detection reagent layer.

Any known chelating agents may be used, as far as they do not form coordination bonds with $Fe^{2+}$ and have specific affinity with $Cu^{2+}$ to form coordination bonds. However, it is desirous to use such a chelating agent that forms a complex with $Cu^{2+}$ having an absorption spectrum peak which is not overlapped with the absorption spectrum peak of the $Fe^{2+}$/Nitro-PAPS complex. It is preferable that the $Cu^{3+}$/chelate complex has no or negligible absorption at least at the wavelength used in the colorimetric measurement.

Examples of such $Cu^{2+}$-specific chelating agent are as follows.

Basocuproine: $\lambda_{max}=479$ nm, $\epsilon=1.4\times10^4$ (mol$^{-1}$ cm$^{-1}$).

Basocuproine disulfonic acid, disodium salt: $\lambda_{max}=483$ nm, $\epsilon=1.2\times10^4$ (mol$^{-1}$ cm$^{-1}$).

Neocuproine: $\lambda_{max}=454$ nm, $\epsilon=8\times10^4$ (mol$^{-1}$ cm$^{-1}$).

When overlapping of the absorption spectra is not negligible, a light-shielding layer may be interposed between the detection reagent layer and the pre-treating layer to shield the coloring by the $Cu^{2+}$-chelate complex.

When the color by the $Fe^{2+}$/Nitro-PAPS complex is determined by inspecting the reflected light from the light-transmitting support side, such a light-shielding layer shields not only the color by the $Cu^{2+}$/chelate complex in the pre-treating layer but also the color of the sample (particularly, the red color of hemoglobin when whole blood is used as the sample) spotted on the analysis element, and serves as a light reflecting layer or background layer. The light-shielding layer may be preferably a water permeable layer containing fine particle of a white light-reflecting material, such as titanium dioxide or barium sulfate, dispersed evenly within a binder material, such as a hydrophilic polymer having a membrane-forming capability. Preferable binder materials include, for example, gelatin, derivatives of gelatin and polyacrylamide. In lieu of the provision of such a separate light-shielding layer, white light-reflecting fine particles (e.g. titanium dioxide) may be contained in the pre-treating layer so that the pre-treating layer exhibits the light-shielding function.

(4-2) Reducing Agent for Reducing $Fe^{3+}$:

A reducing agent may be contained in the pre-treating layer to reduce ferric ions ($Fe^{3+}$) in the sample to ferrous ions ($Fe^{2+}$) which can form a complex with Nitro-PAPAS. For example, the iron ion in transferrin of the blood serum is trivalent $Fe^{3+}$ which can not be combined with Nitro-PAPS even when it is dissociated from transferrin at the pH value of the analysis element of the invention. However, by reducing $Fe^{3+}$ to ferrous ion ($Fe^{2+}$) by the addition of a reducing agent, $Fe^{3+}$ is converted to $Fe^{2+}$ in the analysis element to be analyzed by the analysis element of the invention. Accordingly, the analysis element of the invention can be used not only for the analysis of $Fe^{2+}$ but also for the analysis of $Fe^{3+}$ or the analysis of total iron ions including both of $Fe^{2+}$ and $Fe^{3+}$. Of course, it is possible to use the analysis element of the invention for the analysis of a sample containing only $Fe^{2+}$. In such a case, any reducing agent for reducing $Fe^{3+}$ to $Fe^{2+}$ need not be contained. However, samples are often allowed to stand for a while prior to test and there is a possibility that $Fe^{2+}$ ions in the samples are spontaneously oxidized to $Fe^{3+}$ during they are left for standing. In view of such circumstances, it is preferable to contain a reducing agent in the pre-treating layer for reducing $Fe^{3+}$ to $Fe^{2+}$, even if a sample containing only $Fe^{2+}$ is analyzed.

A proper reducing agent may be selected from known reducing agents and used in the present invention. Examples of well-known reducing agents, which may be used as the reducing agent in the present invention, are hydroxylamine hydrochloric acid, paramethylaminosulfate and ascorbic acid, ascorbylpalmitic acid.

It suffices that such a reducing agent is contained in a layer disposed above the layer containing Nitro-PAPS so that $Fe^{3+}$ ions are reduced to $Fe^{2+}$ before they reach the layer containing Nitro-PAPS. Accordingly, such a reducing agent may be contained in a separate layer different from the layer containing the $Cu^{2+}$-specific chelating agent.

(5) support

A support 10 may be light-nontransmitting (opaque), light-semitransmitting (translucent) or light-transmitting (transparent). It is generally preferred that the support 10 is light-transmitting and water-impermeable.

Preferable examples of light-transmitting and water-impermeable materials for the support 10 include polyethylene terephthalate and polystyrene. In order that the support 10 is firmly adhered to the hydrophilic layer, the support 10 may be coated with an undercoating or the surface thereof is subjected to hydrophilization treatment.

(6) pH Buffer

A pH buffer composition is contained in the analysis element of the invention so that the pH value of the element is kept within a range (pH 3.0 to 5.0) in which the chelating agent Nitro-PAPS forms a complex with $Fe^{2+}$ and scarcely forms a complex with $Zn^{2+}$. Meanwhile, the ratio between the efficiency for detecting the $Zn^{2+}$ complex and that for detecting the $Fe^{2+}$ complex at 600 nm is about 1:100. By addition of such a pH buffer composition, the interference by $Zn^{2+}$ ion can be expelled satisfactorily.

In order to dissociate $Fe^{3+}$ combined to the serum transferrin at a sufficiently high rate, pH value may be kept at pH 4.0 to 5.0. Accordingly, when the analysis element of the invention is used for the analysis of serum transferrin, the pH buffer contained in the element is selected so that the pH value of the element is kept within the pH range of from 4.0 to 5.0.

The pH buffer is contained preferably in the detection reagent layer or the coloring reagent layer so that the pH value of the detection reagent layer or the coloring reagent layer, within which the chelating agent Nitro-PAPS reacts with ferrous ions, is kept within a pH range of 3.0 to 5.0, preferably about 4.0 to about 5.0. However, the pH buffer may be contained in another layer, as far as it is entrained by the aqueous sample liquid to keep the pH value of the detection reagent layer within the desired pH range. Accordingly, the pH buffer may be contained in a layer other than the detection reagent layer, for example, the pre-treating layer, spreading layer or light-reflecting layer. Alternatively, the pH buffer may be contained in a separate water permeable layer.

Examples of the pH buffer compositions which may be used in the present invention are those described in "KAGAKU BINRAN, KISO-HEN", edited by Japanese Chemical Society, published by Maruzen, Tokyo, pages 1312-1320 (1966); those described in "Data for Biochemical Research", 2nd Edition, edited by R. M. C. Dawson et al., published by Oxford at the Clarendon Press (1969), pages 476 to 508; and those described in "Analytical Biochemistry", 104, 300-310 (1980).

Specific examples of the pH buffer system for keeping the pH value within about 3.0 to about 5.0 are buffer systems containing Tris(hydroxymethyl)aminomethane; buffer systems containing phosphates; buffer systems containing borates; buffer systems containing citric acid or citrates; buffer systems containing glycine; buffer systems containing maleic acid, succinic acid, malonic acid, tartaric acid, glutaric acid, barbituric acid, benzoic acid, oxalic acid, fumaric acid, maleic acid, 3,3-dimethylglutaric acid, N,N-bis(2-hydroxyethyl)glycine (Bicine) or N-2-hydroxyethylpiperazine-N'-2-ethanesulfonic acid (HEPES) and an acid, alkali or salt combined with any of the aforementioned acids. Specific examples of preferable buffer are maleic acid, succinic acid, malonic acid, tartaric acid, glutaric acid, 3-3-dimethylglutaric acid, potassiumdihydrogen phosphate/disodiumhydrogen phosphate, Tris-sodium borate, Tris-sodium borate/EDTA disodium salt, Tris-citric acid, acetic acid/sodium acetate, sodium dihydrogen citrate, Bicine and HEPES.

(7) Process for Preparing the Analysis Element

The dry analysis element of the invention may be prepared by the known process described, for example, in the specifications of the prior patents referred to hereinbefore.

It is preferred for the convenience of preparation, packaging, transportation, storage and measuring operation that the analysis element of the invention is cut to a small piece, for example, a square piece having a side length of about 15 mm to about 30 mm or a circular disk having a substantially same area, and the thus cut piece is contained in a slide frame to prepare a slide for chemical analysis, such slide frame as disclosed in Japanese Patent publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent Publication No. 63452/1982, Unexamined Japanese Utility Model Publication No. 32350/1983 and Unexamined Japanese Patent Publication No. 501144/1983 (corresponding to International Publication No. WO 83/00391). For the convenience in some uses, the analysis element may be formed in a tape shape which is contained in a cassette or magazine, or cut pieces thereof may be attached to or contained in cards having small openings.

(8) Method of Analysis

The dry analysis element of the invention may be used for the qualitative or quantitative analysis of iron ions, particularly ferrous ions, in a living fluids of human being or aminals. Samples to be analyzed by the use of the dry analysis element of the invention include whole blood, blood plasma, blood serum, lymph, bile, urine, spinal fluid, saliva, sweat and dejecta. However, samples are not limited to those described above. For example, liquefied samples taken from the tissues of human being or animals, such as skeletal muscles, heart, kidney, lung, brain, spine or skin, can also by analyzed Furthermore, the dry analysis element of the invention can be also used for the analysis of iron ion content in boiler water, waste water, etc.

Iron ions in a liquid sample may be quantitatively analyzed by the dry analysis element of the invention by an operation similar to those described in the specifications of the prior patents referred to herein In detail, about 5 $\mu$l to about 200 $\mu$l of an aqueous sample liquid is spotted on the pre-treating layer 14, the analysis element being allowed to stand at a constant temperature for a predetermined time (incubation), and then the coloring or color change in the element is determined by measuring the reflected light through the light transmitting support. The content of iron ions in the sample can be determined colorimetrically by referring to a calibration curve which has been prepared by plotting the coloring or color change caused by spotting standard solutions. By spotting a constant volume of a liquid sample and by setting the time and temperature for incubation to a constant time and temperatur, quantitative analysis of high accuracy may be realized.

Measurement can be effected by an extremely simple operation by using the chemical analyzer disclosed, for example, in Unexamined Japanese Patent Publication Nos. 125543/1985, 220862/1985, 294367/1986 and 161867/1983 (the last-mentioned Publication corresponding to U.S. Pat. No. 4,424,191) to realize a quantitative analysis at a high accuracy.

Semi-quantitative analysis may be conducted by judging the degeree of coloring by naked eye if such visual judgement is adequate for the object and the required accuracy.

The dry analysis element of the invention may be cut to a test piece which is dipped directly into a sample liquid to read the result qulitatively.

EXAMPLE 1

A dry analysis element for the analysis of iron ions in a blood serum was prepared in accordance with the formulation as set forth in Table 1.

The numerals set forth in the rightmost column in Table 1 show preferred ranges of coverage.

TABLE 1

| | | Coverage (g/m²) | Preferred Range (g/m²) |
|---|---|---|---|
| Spreading Layer | Tricot knitted fabric (Thickness: about 250 um) prepared by knitting (at 36 gages) a 50 deniel polyethylene terephthalate spun yarn | | |
| Adhesive Layer | Deionized Gelatin | 2 | 1 to 5 |
| Pre-treating Layer | Polyvinylpyrrolidone (Binder; Average Molecular Weight: about 1,200,000) | 5.0 | 1 to 10 |
| | p-Methylaminophenol Sulfate (Reducing Agent) | 2 | 0.5 to 10 |
| | Basocuproine (Chelating Agent for $Cu^{2+}$) | 1.0 | 0.5 to 10 |
| Detection Reagent Layer: | | | |
| Diffusion-Preventing Layer | Cationic Polymer, Polymer #5 | 2.0 | 1.0 to 10 |
| | Acetic Acid/Sodium Acetate (pH 4.3; Buffer) | 3 | 0.5 to 10 |
| | Nonylphenoxypolyethoxyethanol (Average Content of Oxyethylene Unit: 9 to 10; Surface Active Agent) | 0.5 | 0.2 to 4 |
| | Deionized Gelatin | 5 | 3 to 15 |
| | Bis[(vinylsulfonylmethylcarbonylamino]methane (Hardener) | 0.05 | 0.01 to 0.5 |
| Detection Reagent Layer | Nitro-PAPS | 0.5 | 0.05 to 5 |
| | Acetic Acid/Sodium Acetate (pH 4.3; Buffer) | 3 | 0.5 to 10 |
| | Nonylphenoxypolyethoxyethanol (Average Content of Oxyethylene Unit: 9 to 10; Surface Active Agent) | 0.5 | 0.2 to 4 |
| | Deionized Gelatin | 5 | 3 to 15 |
| | Bis[(vinylsulfonylmethylcarbonylamino]methane (Hardener) | 0.05 | 0.01 to 0.5 |
| Support | Polyethylene terephthalate | | |

EXAMPLE 2

The dry analysis element prepared by Example 1 was appraised by the following procedure.

Standard solutions in 1 mM HCl having different concentrations of ferrous ions were prepared.

10 μl for each of these standard solutions were spotted on the spreading layer and allowed to stand for 5 minutes, and then the optical density of the reflected light through the support layer was measured at a wavelength of 577 nm. The results are as follows.

TABLE 2

| Concentration of $Fe^{2+}$ | OD at 577 nm |
|---|---|
| 100 μg/dl | 0.630 |
| 200 μg/dl | 0.660 |
| 400 μg/dl | 0.720 |
| 800 μg/dl | 0.836 |

As shown in Table 2, $Fe^{2+}$ ions could be detected in such a way that the line drawn by plotting the optical density had satisfactory linearity.

In the dry analysis element of the invention for the analysis of iron ions, interference by the presence of $Cu^{2+}$ ions is effectively excluded by the addition of a chelating agent having specific affinity with $Cu^{2+}$ ions. On the other hand, the pH value of the element is kept within the range of from 3.0 to 5.0, at which the used chelating agent Notro-PAPS does not form a complex with $Zn^{2+}$ ions, whereby interference by the presence of $Zn^{2+}$ ions is excluded. Accordingly, the dry analysis element of the invention is improved in selectivity for iron ions to exclude interferences due to the presence of hindering $Cu^{2+}$ and $Zn^{2+}$ ions. The dry analysis element of the invention is improved in sensitivity since Nitro-PAPS is used as the chelating agent. The reaction rate with $Fe^{2+}$ ions is high enough to give the result promptly.

What is claimed is:

1. A dry analysis element for the analysis of iron ion, comprising:
   (a) a detection reagent layer containing Nitro-PAPS acting as a chelating agent for iron ion and a cationic compound;
   (b) a pre-treating layer containing a chelating agent specifically forming a coordination compound with cupric ion; and
   (c) a pH buffer for keeping the pH value of said detection reagent layer within the range of from pH 3.0 to pH 5.0, said pH buffer being contained in either one of said detection reagent layer or said pre-treating layer or contained in another layer in said dry analysis element.

2. The dry analysis element according to claim 1, wherein said pre-treating layer further contains a reducing agent for reducing ferric ion to ferrous ion.

3. The dry analysis element according to claim 1, wherein said pH buffer is contained in said detection reagent layer.

4. The dry analysis element according to claim 1, wherein said detection reagent layer includes a coloring reagent layer containing the Nitro-PAPS acting as a chelating agent, and a diffusion-preventing layer which contains the cationic compound laminated on said coloring reagent layer.

5. The dry analysis element according to claim 1, further comprising a light-shielding layer disposed between said detection reagent layer and said pre-treating layer.

6. A dry analysis element for the analysis of iron ion, comprising:

(a) a light-transmitting support;
(b) a detection reagent layer containing Nitro-PAPS acting as a chelating agent for iron ion and a cationic compound;
(c) a pre-treating layer containing a chelating agent specifically forming a coordination compound with cupric ion;
(d) a spreading layer; and
(e) a pH buffer for keeping the pH value of said detection reagent layer within the range of from pH 3.0 to pH 5.0, said pH buffer being contained in any one of said detection reagent layer, said pre-treating layer and said spreading layer or contained in another layer in said dry analysis element.

7. The dry analysis element according to claim 6, wherein said pre-treating layer further contains a reducing agent for reducing ferric ion to ferrous ion.

8. The dry analysis element according to claim 6, wherein said pH buffer is contained in said detection reagent layer.

9. The dry analysis element according to claim 6, wherein said detection reagent layer includes a coloring reagent layer containing the Nitro-PAPS acting as a chelating agent, and a diffusion-preventing layer which contains the cationic compound laminated on said coloring reagent layer.

10. The dry analysis element according to claim 6, further comprising a light-shielding layer disposed between said detection reagent layer and said pre-treating layer.

* * * * *